United States Patent
Herlihy et al.

(10) Patent No.: US 7,101,998 B2
(45) Date of Patent: Sep. 5, 2006

(54) FUSED RING COMPOUNDS, AND THEIR USE AS CATIONIC PHOTOINITIATORS

(75) Inventors: Shaun Lawrence Herlihy, Chatham (GB); Robert Stephen Davidson, Leicester (GB); Brian Rowatt, Maidstone (GB)

(73) Assignee: Sun Chemical Corporation, (JP)

( * ) Notice: Subject to any disclaimer, the term of this patent is extended or adjusted under 35 U.S.C. 154(b) by 0 days.

(21) Appl. No.: 10/505,650

(22) PCT Filed: Feb. 26, 2003

(86) PCT No.: PCT/US03/06106

§ 371 (c)(1),
(2), (4) Date: Apr. 21, 2005

(87) PCT Pub. No.: WO03/072567

PCT Pub. Date: Sep. 4, 2003

(65) Prior Publication Data

US 2005/0176969 A1  Aug. 11, 2005

(30) Foreign Application Priority Data

Feb. 26, 2002  (GB) ................... 0204467.5

(51) Int. Cl.
| | |
|---|---|
| C07D 279/28 | (2006.01) |
| C07D 279/20 | (2006.01) |
| C07D 327/08 | (2006.01) |
| C07D 335/16 | (2006.01) |
| C07D 335/12 | (2006.01) |
| C07D 333/76 | (2006.01) |
| C07D 339/08 | (2006.01) |
| C08F 20/50 | (2006.01) |

(52) U.S. Cl. ............... 544/38; 544/35; 549/16; 549/17; 549/23; 549/26; 549/27; 549/43; 524/80; 524/82; 524/83; 524/84; 524/457; 252/182.17

(58) Field of Classification Search ............ 549/16, 549/17, 23, 26, 27, 43; 544/35, 38; 524/80, 524/82, 83, 84, 457; 252/182.17
See application file for complete search history.

(56) References Cited

U.S. PATENT DOCUMENTS 4,161,478 A   7/1979  Crivello ................. 260/327 B 2004/0242901 A1*  12/2004  Norcini et al. ............ 549/3
2005/0064333 A1*  3/2005  Crivello .................. 430/270.1

FOREIGN PATENT DOCUMENTS

WO    WO 03/002557 A1 *  5/2002

OTHER PUBLICATIONS

Crivello et al, J. of Polymer Science, Part A:Polymer Chemistry, 40(20), p. 3465-3480 (Sep. 2002).*
M. Kim and K. Kim; Synthesis of 2,3,8,9-Dibenzo-5,6-(substituted)benzo-1,4-dithio-7-oxacyclonona-2,5,8-trienes and Some Electrophilic Substitution Reactions; J. Heterocyclic Chem., 1998; vol. 35; pp. 235-247.

\* cited by examiner

*Primary Examiner*—Bernard Dentz
(74) *Attorney, Agent, or Firm*—Dickstein Shapiro LLP

(57) ABSTRACT

Compounds of formula (I):

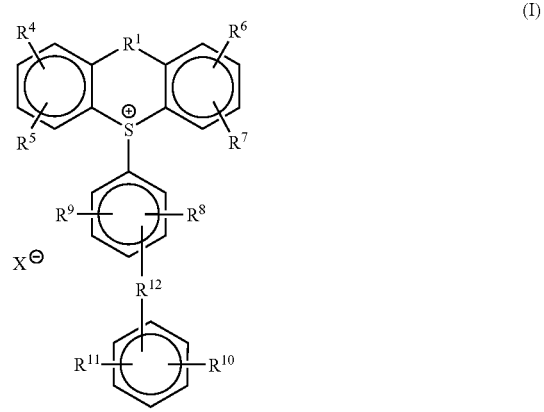

[in which: $R^1$ represents a direct bond, an oxygen atom, a group $>CH_2$, a sulphur atom, a group $>C=O$, a group $-(CH_2)_2-$ or a group of formula $-N-R^a$, where $R^a$ is hydrogen or an alkyl; $R^4$, $R^5$, $R^6$ and $R^7$ are each hydrogen or various groups or atoms; $R^8$, $R^9$, $R^{10}$ and $R^{11}$ are each hydrogen, hydroxy, or alkyl; or $R^9$ and $R^{11}$ form a fused ring system with the benzene rings to which they are attached; $R^{12}$ is a direct bond, oxygen atom or methylene; and $X^-$ is an anion; and esters thereof] are useful as cationic photoinitiators, especially for use in surface coating applications, such as printing inks and varnishes, and which are intended to be cured by polymerisation initiated by radiation.

21 Claims, No Drawings

FUSED RING COMPOUNDS, AND THEIR USE AS CATIONIC PHOTOINITIATORS

This application is a national stage entry of PCT/US03/06106 filed Feb. 26, 2003.

The present invention relates to a series of novel fused ring, especially thioxanthone, thianthrene, dibenzothiophene, thioxanthene, phenoxathiin or phenothiazine, compounds which are useful as cationic photoinitiators, especially for use in surface coating applications, such as printing inks and varnishes, and which are intended to be cured by polymerisation initiated by radiation.

Photocurable compositions are cured by exposure to radiation, usually ultraviolet radiation, and include for example, lacquers which may be applied to wood, metal or similar substrates by suitable techniques such as roll coating or curtain coating. They may also be formulated as inks, for example to be applied by techniques such as letterpress, offset lithography, rotogravure printing, silk screen printing, inkjet or flexographic printing. Printing, depending on the particular printing technique, is applicable to a wide range of substrates which include paper, board, glass, plastics materials or metals. Other application areas will include adhesives, powder coatings, circuit boards and microelectronic products, sterolithography, composites, optical fibres and liquid crystals.

Initiation of polymerisation in a monomer or prepolymer may be effected in a number of ways. One such way is by irradiation, for example with ultraviolet radiation, in which case it is normally necessary that the polymerisable composition should contain an initiator, commonly referred to as a "photoinitiator", or alternatively by an electron beam. There are two main types of curing chemistry which can be used in this process; free radical and cationic. Although cationic curing has many advantages, its disadvantages, particularly with regard to the photoinitiators used, leads it to be used only in a minority of applications. Most frequently used cationic initiators are either organic iodonium or sulphonium salts.

Briefly, the mechanism by which a sulphonium cationic initiator acts when irradiated is that it forms an excited state which then breaks down to release a radical cation. This radical cation reacts with the solvent, or another hydrogen atom donor, generating a protonic acid. The active species is the protonic acid. However, amongst the breakdown products of sulphonium salts are aromatic sulphides, such as diphenyl sulphide, which are malodorous and can be a health hazard, and lower aromatic hydrocarbons, such as benzene, which are potentially carcinogenic. Many of the commonly used iodonium salts break down to give volatile species such as benzene, toluene or isobutyl benzene. This places severe restrictions upon the applications for which such cationic photoinitiators can be used. For example, they cannot be used in printing inks on packaging intended for food and, in some cases, cannot be used at all where the packaging is to be handled by the consumer. Indeed, as the industry becomes ever more conscious of health matters, it is increasingly difficult to use such compounds at all.

However, this, although important, is not the only constraint upon the choice of compound to be used as a cationic photoinitiator. Even without consideration of the health issues, the cleavage products of the known cationic photoinitiators are malodorous, and it is highly desirable that unpleasant odours should be minimised. This leads to a desire that the cleavage products should be relatively non-volatile and non-odorous. The cationic photoinitiators must, of course, also be sufficiently stable, both as isolated compounds and when in the uncured coating formulation. They must also be soluble in or miscible with other components of the uncured coating formulation. Finally, they should be able to absorb radiation over a suitable and sufficiently wide range of wave lengths, ideally without the use of a sensitiser.

What is more, the nature of the cationic photoinitiator can have a major impact on the properties of the cured coating. The cationic photoinitiator should produce a coating which is fully cured, hard and resistant to common solvents and abuse.

Finally, there are a number of practical problems associated with the manufacture of the compounds used as cationic photoinitiators, including the necessity that they should be relatively easy and inexpensive to manufacture.

Thus, it would be desirable to provide a cationic photoinitiator which does not generate malodorous or toxic by-products upon radiation cure, particularly diphenyl sulphide and benzene, and which possesses the following properties: good solubility, good cure performance, good adhesion to substrates and reasonable cost.

Not surprisingly, complying with all of these, often conflicting, requirements is not easy, and we are not aware of any completely satisfactory commercial solution available until now.

However, we have now discovered a series of new compounds, including thioxanthone derivatives, many of which have the advantages of good solubility in the coating composition combined with excellent cure. These compounds have a biphenylyl or phenoxy- or benzyl-substituted phenyl group attached to the thioxanthone or analogous ring. In addition, the potential by-products of these new compounds would be thioxanthone derivatives typical of those used widely in free-radical curing inks for food packaging, and biphenyl, which is itself an approved antioxidant food additive in Europe.

Compounds of this general type are covered in general terms in U.S. Pat. No. 4,161,478, although these lack the solubility of the compounds of the present invention, and the US Patent does not specifically disclose such compounds. Indeed, the US Patent is silent on the nature of the ring system attached to the thioxanthone or analogous ring system, although we have found that the nature of this ring system is highly important to the achievement of good solubility and cure. Also, a biphenyl-substituted dibenzothiophene compound is disclosed by Sato et al. [Phosphorus, Sulfur, and Silicon, 1994, Vol 95–96, pp 447–448], but no use is suggested for the resulting compounds. Similarly, a biphenyl-substituted thianthrene is disclosed by Kim and Kim (J. Heterocyclic Chem., 1998, Vol 35, pages 235–247), but this has only been prepared as a salt with a perchlorate anion, and no use is suggested for the compound other than in further synthetic chemistry.

Thus, the present invention consists in compounds of formula (I):

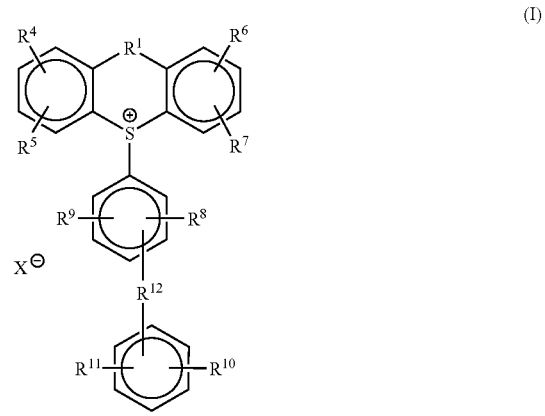

in which:

R$^1$ represents a direct bond, an oxygen atom, a group >CH$_2$, a sulphur atom, a group >C=O, a group —(CH$_2$)$_2$— or a group of formula —N—R$^a$, where R$^a$ represents a hydrogen atom or an alkyl group having from 1 to 12 carbon atoms;

R$^4$, R$^5$, R$^6$ and R$^7$ are individually the same or different and each represents a hydrogen atom or a group or atom selected from substituents α, defined below, provided that, when R$^1$ represents a group >C=O, then at least one of R$^4$, R$^5$, R$^6$ and R$^7$ represents a substituent α;

R$^8$, R$^9$, R$^{10}$ and R$^{11}$ are individually the same or different and each represents a hydrogen atom, a hydroxy group, or an alkyl group having from 1 to 4 carbon atoms;

or R$^9$ and R$^{11}$ are joined to form a fused ring system with the benzene rings to which they are attached;

R$^{12}$ represents a direct bond, an oxygen atom or a methylene group;

said substituents α are: an alkyl group having from 1 to 20 carbon atoms, an alkoxy group having from 1 to 20 carbon atoms, an alkenyl group having from 2 to 20 carbon atoms, a halogen atom, a nitrile group, a hydroxyl group, an aryl group having from 6 to 10 carbon atoms, an aralkyl group having from 7 to 13 carbon atoms, an aryloxy group having from 6 to 10 carbon atoms, an aralkyloxy group having from 7 to 13 carbon atoms, an arylalkenyl group having from 8 to 12 carbon atoms, a cycloalkyl group having from 3 to 8 carbon atoms, a carboxy group, a carboxyalkoxy group having from 2 to 7 carbon atoms, an alkoxycarbonyl group having from 2 to 7 carbon atoms, an aryloxycarbonyl group having from 7 to 13 carbon atoms, an alkylcarbonyloxy group having from 2 to 7 carbon atoms, an alkanesulphonyl group having from 1 to 6 carbon atoms, an arenesulphonyl group having from 6 to 10 carbon atoms, an alkanoyl group having from 1 to 6 carbon atoms or an arylcarbonyl group having from 7 to 11 carbon atoms; and X$^-$ represents an anion, provided X$^-$ does not represent an alkoxy, hydroxyalkoxy or aryloxy group when R$^1$ represents a direct bond;

and esters thereof.

These compounds are useful as photoinitiators for use in energy, e.g. UV, curable coating compositions, including varnishes, lacquers and printing inks, most especially printing inks.

The compounds of the present invention may, as described above, be used as cationic photoinitiators for radiation-curable coating compositions. Thus, the present invention also provides an energy-curable composition comprising: (a) a polymerisable monomer, prepolymer or oligomer, especially a material which undergoes acid-catalysed ring opening polymerisation, e.g. an epoxide (oxirane) or oxetane, or an ethylenically unsaturated material, such as vinyl or propenyl ethers and (b) a cationic photoinitiator which is a compound of formula (I), as defined above, or an ester thereof.

The invention still further provides a process for preparing a cured polymeric composition by exposing a composition of the present invention to curing energy, preferably ultraviolet radiation.

In the compounds of the present invention, we prefer those compounds of formula (I) in which R$^1$ represents a group >C=O, a sulphur atom or a direct bond, and especially those in which R$^1$ represents a group >C=O.

More preferred are those compounds of formula (I) in which the residue of formula (A):

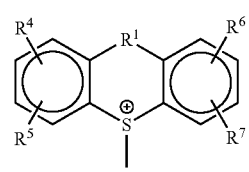

(A)

is a residue of substituted or unsubstituted thianthrene, dibenzothiophene, thioxanthone, thioxanthene, phenoxathiin or phenothiazine, especially those in which said residue is a substituted thioxanthone.

Where R$^4$, R$^5$, R$^6$ or R$^7$ represents an alkyl group having from 1 to 20, preferably from 1 to 10, more preferably from 1 to 6 and most preferably from 1 to 3, carbon atoms, this may be a straight or branched chain group, and examples of such groups include the methyl, ethyl, propyl, isopropyl, butyl, isobutyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl, isohexyl, heptyl, octyl, nonyl, decyl, dodecyl, tridecyl, pentadecyl, octadecyl, nonadecyl and icosyl groups, but preferably the methyl, ethyl, propyl, isopropyl and t-butyl groups, and most preferably the ethyl or isopropyl group. R$^a$ may be any of the groups having from 1 to 12 carbon atoms exemplified above, especially those having from 1 to 6 carbon atoms, and preferably the methyl group.

Where R$^4$, R$^5$, R$^6$ or R$^7$ represents an alkoxy group having from 1 to 20, preferably from 1 to 10, more preferably from 1 to 6 and most preferably from 1 to 3, carbon atoms, this may be a straight or branched chain group, and examples of such groups include the methoxy, ethoxy, propoxy, isopropoxy, butoxy, isobutoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy, isohexyloxy, heptyloxy, 2-ethylhexyloxy, octyloxy, nonyloxy, decyloxy, dodecyloxy, tridecyloxy, pentadecyloxy, octadecyloxy, nonadecyloxy and icosyloxy groups, but preferably the methoxy, ethoxy, t-butoxy and 2-ethylhexyloxy groups, and most preferably the 2-ethylhexyloxy group.

Where R$^4$, R$^5$, R$^6$ or R$^7$ represents an alkenyl group having from 2 to 20, preferably from 2 to 10, more preferably from 2 to 6 and most preferably from 2 to 4, carbon atoms, this may be a straight or branched chain group, and examples of such groups include the vinyl, 1-propenyl, allyl, isopropenyl, methallyl, butenyl, pentenyl, hexenyl, heptenyl, octenyl, nonenyl, decenyl, dodecenyl, tridecenyl, pentadecenyl, octadecenyl, nonadecenyl and icosenyl groups, but preferably the allyl, methallyl and butenyl groups, and most preferably the allyl group.

Where R$^4$, R$^5$, R$^6$ or R$^7$ represents a halogen atom, this may be, for example, a fluorine, chlorine, bromine or iodine atom, preferably a chlorine atom.

Where R$^4$, R$^5$, R$^6$ or R$^7$ represents an aryl group, this has from 6 to 10 carbon atoms in one or more aromatic carbocyclic rings (which, if there are more than one, may be fused together). Such a group may be substituted or unsubstituted, and, if substituted, the substituent(s) is preferably an alkyl or alkoxy group (as defined above), or an alkoxycarbonyl group (as defined below). Preferred aryl groups are the phenyl and naphthyl (1- or 2-) groups, the phenyl group being most preferred.

Where $R^4$, $R^5$, $R^6$ or $R^7$ represents an aryloxy group, this may be any of the aryl groups above bonded to an oxygen atom, and examples include the phenoxy and naphthyloxy groups.

Where $R^4$, $R^5$, $R^6$ or $R^7$ represents an aralkyl group, this is an alkyl group having from 1 to 4 carbon atoms which is substituted by one or two aryl groups as defined and exemplified above. Examples of such aralkyl groups include the benzyl, α-phenylethyl, β-phenylethyl, 3-phenylpropyl, 4-phenylbutyl, diphenylmethyl, 1-naphthylmethyl and 2-naphthylmethyl groups, of which the benzyl group is preferred.

Where $R^4$, $R^5$, $R^6$ or $R^7$ represents an aralkyloxy group, this may be any of the aralkyl groups above bonded to an oxygen atom, and examples include the benzyloxy, α-phenylethoxy, β-phenylethoxy, 3-phenylpropoxy, 4-phenylbutoxy, diphenylmethoxy, 1-naphthylmethoxy and 2-naphthylmethoxy groups, of which the benzyloxy group is preferred.

Where $R^4$, $R^5$, $R^6$ or $R^7$ represents an arylalkenyl group having from 8 to 12 carbon atoms, the aryl and alkenyl parts of this group may be as defined and exemplified above for the respective component parts. Specific examples of such groups are the styryl and cinnamyl groups.

Where $R^4$, $R^5$, $R^6$ or $R^7$ represents a cycloalkyl group having from 3 to 8 carbon atoms, this may be, for example, the cyclopropyl, cyclobutyl, cyclopentyl, cyclohexyl, cycloheptyl or cyclooctyl group.

Where $R^4$, $R^5$, $R^6$ or $R^7$ represents a carboxyalkoxy group, this may be any of the alkoxy groups having from 1 to 6 carbon atoms described above which is substituted by a carboxy group. Preferred examples include the carboxymethoxy, 2-carboxyethoxy and 4-carboxybutoxy groups, of which the carboxymethoxy group is preferred.

Where $R^4$, $R^5$, $R^6$ or $R^7$ represents an alkoxycarbonyl group, this has from 1 to 6 carbon atoms in the alkoxy part, and thus a total of from 2 to 7 carbon atoms. It may be a straight or branched chain group, and examples of such groups include the methoxycarbonyl, ethoxycarbonyl, propoxycarbonyl, isopropoxycarbonyl, butoxycarbonyl, isobutoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups, but preferably the methoxycarbonyl, ethoxycarbonyl and t-butoxycarbonyl groups, and most preferably the methoxycarbonyl or ethoxycarbonyl group.

Where $R^4$, $R^5$, $R^6$ or $R^7$ represents an aryloxycarbonyl group having from 7 to 13 carbon atoms, the aryl part of this may be any of the aryl groups defined and exemplified above. Specific examples of such groups include the phenoxycarbonyl and naphthyloxycarbonyl groups.

Where $R^4$, $R^5$, $R^6$ or $R^7$ represents an alkylcarbonyloxy group having from 2 to 7 carbon atoms, this may be any of the alkoxycarbonyl groups defined and exemplified above bonded to an oxygen atom.

Where $R^4$, $R^5$, $R^6$ or $R^7$ represents an alkanesulphonyl group, this has from 1 to 6 carbon atoms and is a straight or branched chain group. Examples of such groups include the methanesulphonyl, ethanesulphonyl, propanesulphonyl, isopropanesulphonyl, butanesulphonyl, isobutanesulphonyl, t-butanesulphonyl, pentanesulphonyl and hexanesulphonyl groups, of which the methanesulphonyl group is preferred.

Where $R^4$, $R^5$, $R^6$ or $R^7$ represents an arenesulphonyl group, the aryl part may be as defined and exemplified above, and examples include the benzenesulphonyl and p-toluenesulphonyl groups.

Where $R^4$, $R^5$, $R^6$ or $R^7$ represents an alkanoyl group having from 1 to 6 carbon atoms, and preferably from 1 to 4 carbon atoms, this may be a straight or branched chain group, and examples include the formyl, acetyl, propionyl, butyryl, isobutyryl, pivaloyl, valeryl, isovaleryl, and hexanoyl groups, of which the acetyl group is most preferred;

Where $R^4$, $R^5$, $R^6$ or $R^7$ represents an arylcarbonyl group, the aryl part has from 6 to 10, more preferably 6 or 10, and most preferably 6, ring carbon atoms and is a carbocyclic group, which is unsubstituted or has from 1 to 5, preferably from 1 to 3 substituents, as defined and exemplified above. The preferred groups are the benzoyl and naphthoyl groups.

We particularly prefer those compounds of formula (I) in which $R^4$, $R^5$, $R^6$ and $R^7$ are individually the same or different and each represents a hydrogen atom, an alkyl group having from 1 to 10 carbon atoms, an alkoxy group having from 1 to 10 carbon atoms, a halogen atom, or a cycloalkyl group having from 3 to 8 carbon atoms, more especially those in which two or three of $R^4$, $R^5$, $R^6$ and $R^7$ represent hydrogen atoms, and most preferably those in which one or two of $R^4$, $R^5$, $R^6$ and $R^7$ represents an ethyl or isopropyl group. The most preferred compounds are those in which one or two of $R^4$, $R^5$, $R^6$ and $R^7$ represent ethyl groups or in which one of $R^4$, $R^5$, $R^6$ and $R^7$ represents an isopropyl group and the others represent hydrogen atoms.

Where $R^8$, $R^9$, $R^{10}$ or $R^{11}$ represents an alkyl group, this may be a straight or branched chain alkyl group having from 1 to 4 carbon atoms, and examples include the methyl, ethyl, propyl, isopropyl, butyl, isobutyl and t-butyl groups, of which the methyl group is preferred.

We prefer those compounds of formula (I) in which two, three or four of $R^8$, $R^9$, $R^{10}$ and $R^{11}$ represent hydrogen atoms, and especially those in which all of $R^8$, $R^9$, $R^{10}$ and $R^{11}$ represent hydrogen atoms.

When $R^9$ and $R^{11}$, together with the benzene rings to which they are attached, form a fused ring system, this may be, for example, a biphenylene, fluorene or phenanthrene system, preferably fluorene.

$R^{12}$ may be a direct bond (so that the two groups joined by $R^{12}$ together form a biphenylyl group), an oxygen atom (so that the two groups joined by $R^{12}$ together form a phenoxyphenyl group), or a methylene group (so that the two groups joined by $R^{12}$ together form a benzylphenyl group).

$X^-$ represents an anion. In general, there is no particular limitation on the nature of the anion to be used. However, where the compounds of the present invention are to be used as photoinitiators, the anion should be non-nucleophilic, or essentially non-nucleophilic, as is well known in the art. It should also be relatively bulky. If the compounds are not to be used as photoinitiators, the anion need not meet these requirements. For example, in some cases, it may be desirable not to store the compound in the form of the salt which is ultimately to be used. In that case, it may be preferable to form another salt, and then convert the compound to the desired salt at or close to the point of use. In such a case, it is not necessary that the anion should be non-nucleophilic.

Examples of non-nucleophilic anions are well known to those skilled in the art, and include anions of formula $MZ_n^-$ where M represents a phosphorus, boron, antimony, arsenic, chlorine or carbon atom, Z represents a halogen atom except where M represents a halogen atom, an oxygen atom or a sulphite group, and n is an integer dependent upon the valence of M and Z. Preferred examples of such groups include the $PF_6^-$, $SbF_6^-$, $AsF_6^-$, $BF_4^-$, $B(C_6F_5)_4^-$, $R^aB(Ph)_3^-$ (where $R^a$ represents an alkyl group having from 1 to 6 carbon atoms and Ph represents a phenyl group), $R^bSO_3^-$ (where $R^b$ represents an alkyl or haloalkyl group having from 1 to 6 carbon atoms or an aryl group), $ClO_4^-$ and $ArSO_3^-$ (where Ar represents an aryl group) groups, of which the $PF_6^-$, $SbF_6^-$, $AsF_6^-$, $CF_3SO_3^-$ and $BF_4^-$ groups are preferred and the $PF_6^-$ group is most preferred.

Where the compounds of the present invention contain a carboxy group, i.e. where $R^4$, $R^5$, $R^6$ or $R^7$ represents a carboxy or carboxyalkoxy group, the resulting compounds may form esters, and these esters also form a part of the present invention. There is no particular limitation on the nature of the ester, other than those constraints well known to those skilled in the art, and preferred examples of esters include the alkyl esters, particularly those having from 1 to 12 carbon atoms, such as those containing the $C_1$–$C_{12}$ alkyl groups, and those derived from a polyalkylene glycol ether ester (especially the $C_1$–$C_4$ alkyl ethers), such as esters containing groups of formula:

—[OR$^{13}$]$_x$OR$^{14}$ where $R^{13}$ represents an alkylene group having from 1 to 8 carbon atoms, $R^{14}$ represents an alkyl group having from 1 to 4 carbon atoms, and x is a number from 2 to 20, preferably from 5 to 10. More preferred are groups of formula:

—[OCH$_2$CHR$^{15}$]$_x$OR$^{14}$ where $R^{14}$ and x are as defined above and $R^{15}$ represents an alkyl group having from 1 to 4 carbon atoms.

Where $R^8$, $R^9$, $R^{10}$ or $R^{11}$ represents a hydroxy group, the resulting compounds may also form esters with acids. Examples of such esters are given in "Protective Groups in Organic Synthesis" by T. W. Greene and P. G. M. Wuts, Second Edition, 1991, published by John Wiley & Sons, Inc.

Any combination of the preferred substituent groups and atoms listed above in respect of $R^1$, $R^4$, $R^5$, $R^6$, $R^7$, $R^8$, $R^9$, $R^{10}$, $R^{11}$, $R^{12}$, is also envisaged by the present invention.

Particularly preferred compounds of the present invention having an especially good combination of good cure and good solubility in coating compositions are those compounds of formula (I) in which:

$R^4$, $R^5$, $R^6$ and $R^7$ are individually the same or different and each represents a hydrogen atom or an alkyl group having from 1 to 4 carbon atoms;

$R^{12}$ represents a direct bond; and $R^8$, $R^9$, $R^{10}$ and $R^{11}$ represent hydrogen atoms.

The compounds of the present invention may be prepared by reacting a sulphoxide corresponding to ring system (A) with the compound corresponding to the biphenylyl, phenoxyphenyl or benzylphenyl ring system in the presence of an acid, as shown in the following scheme:

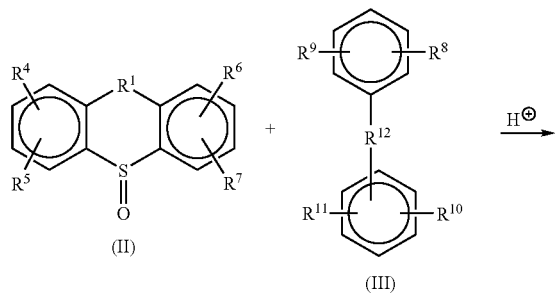

(II) + (III) →$^{H^⊕}$

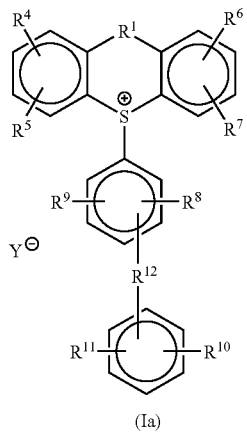

(Ia)

In the above formulae, $R^1$, $R^4$, $R^5$, $R^6$, $R^7$, $R^8$, $R^9$, $R^{10}$ and $R^{11}$ are as defined above, and $Y^-$ represents an anion, which will normally be derived from the reaction. Where any one or more of $R^8$, $R^9$, $R^{10}$, or $R^{11}$ represents a hydroxy group, this is preferably protected, since it otherwise may react with the acid used in the reaction. The nature of the protecting group used is not critical to the invention, and any protecting group known in the art for use in compounds of this type may equally be used here. Examples of suitable protecting groups are described in "Protective Groups in Organic Synthesis" by T. W. Greene and P. G. M. Wuts, Second Edition, 1991, published by John Wiley & Sons, Inc.

The reaction is normally and preferably effected in a solvent, the nature of which is not critical, provided that it has no adverse effect on the reagents or on the reaction and provided that it can dissolve the reagents, at least to some extent. A suitable solvent is acetic acid.

The reaction is also preferably effected in the presence of a strong acid. Preferred is a combination of concentrated sulphuric acid and acetic anhydride.

A suitable reaction temperature is preferably below 15° C.

The sulphoxide of formula (II) may be prepared by well known methods.

Using the reaction scheme above, it is possible to obtain yields in excess of 90% in each reaction step, which assists the economics of the process.

In general, the anion $Y^-$ will not be the anion $X^-$ which it is desired to incorporate in the final product. If so, then the desired anion may be introduced by an anion exchange reaction, as is well known in the field of synthetic chemistry.

Where a protected hydroxy group represented by $R^8$, $R^9$, $R^{10}$, or $R^{11}$ is present, the protecting group may, if desired, be removed by methods well known to those skilled in the art, as described in "Protective Groups in Organic Synthesis" above.

The compounds of the invention may then be separated from the reaction mixture by well known techniques and, if desired, further purified.

The composition of the present invention may be formulated as a printing ink, varnish, adhesive or any other coating composition which is intended to be cured by irradiation, whether by ultraviolet or electron beam. Such compositions will normally contain at least a polymerisable monomer, prepolymer or oligomer, and the cationic photoinitiator of the present invention, but may also include other components well known to those skilled in the art, for example, reactive diluents and, in the case of printing inks, a pigment.

A wide variety of monomers and prepolymers may be subjected to cationic photoinitiation using the compounds of the present invention as photoinitiators, and the nature of the monomers and prepolymers is not critical to the present invention. Such monomers and prepolymers typically contain cationically polymerisable groups, and general examples of such compounds include the epoxides, oxetanes, other cyclic ethers, vinyl compounds (such as vinyl and propenyl ebers, styrene and its derivatives and unsaturated polyesters), unsaturated hydrocarbons, lactones and, in the case of hybrid systems, acrylates and methacrylates.

Typical epoxides which may be used include the cycloaliphatic epoxides (such as those sold under the designations UVR6110 by Union Carbide or UVACURE 1500 by UCB), which are well known to those skilled in the art.

Other epoxy-functional oligomers/monomers which may be used include the glycidyl ethers of polyols [bisphenol A, alkyl diols or poly(alkylene oxides), which be di-, tri-, tetra- or hexa-functional]. Also, epoxides derived by the epoxidation of unsaturated materials may also be used (e.g. epoxidised soybean oil, epoxidised polybutadiene or epoxidised alkenes). Naturally occurring epoxides may also be used, including the crop oil collected from *Vernonia galamensis*.

As well as epoxides, other reactive monomers/oligomers which may be used include the vinyl ethers of polyols [such as triethylene glycol divinyl ether, 1,4-cyclohexane dimethanol divinyl ether and the vinyl ethers of poly(alkylene oxides)]. Examples of vinyl ether functional prepolymers include the urethane-based products supplied by Allied Signal. Similarly, monomers/oligomers containing propenyl ether groups may be used in place of the corresponding compounds referred to above containing vinyl ether groups.

Similarly, compounds bearing oxetane groups may be used in place of the corresponding compounds referred to above containing epoxide groups. A typical oxetane is that derived from trimethylolpropane (3-ethyl-3-hydroxymethyloxetane).

Other reactive species can include styrene derivatives and cyclic esters (such as lactones and their derivatives).

It is also common to include polyols in ultraviolet cationic curable formulations, which promote the cross-linking by a chain-transfer process. Examples of polyols include the ethoxylated/propoxylated derivatives of, for example, trimethylolpropane, pentaerythritol, di-trimethylolpropane, di-pentaerythritol and sorbitan esters, as well as more conventional poly(ethylene oxide)s and poly(propylene oxide)s. Other polyols well known to those skilled in the art are the polycaprolactone diols, triols and tetraols, such as those supplied by Union Carbide.

Additives which may be used in conjunction with the principal components of the coating formulations of the present invention include stabilisers, plasticisers, pigments, waxes, slip aids, levelling aids, adhesion promoters, surfactants and fillers. Also, compounds which act as sensitisers for the photoinitiator, such as thioxanthone (and derivatives), benzophenone (and derivatives), hydroxyalkylphenones, anthracene (and derivatives), perylene, xanthone, pyrene and anthraquinone, may be included.

The compounds of the present invention may be included as photoinitiators in coating formulations such are well known in the art, and the precise composition of such formulations will vary depending upon the other components and the intended use, as is well known. However, a typical formulation for an ink coatable by flexography might be:

| | |
|---|---|
| Pigment | 8–20% |
| Photoinitiator | 2–6% |
| Monomer/prepolymer/oligomer | 30–90% |
| Polyol | 0–30% |
| Additives | 0–10% |

In order to enhance the solubility of the compounds of the present invention in the curable composition, they may first be dissolved in a suitable solvent, for example propylene carbonate.

The invention is further illustrated by the following non-limiting Examples.

EXAMPLE 1

Preparation of isopropylthioxanthone sulphoxide

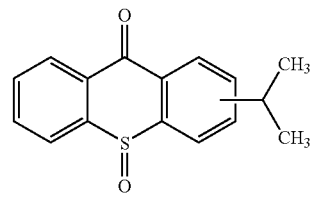

10.0 g of ITX (isopropylthioxanthone) (0.03937 moles) were dissolved in 630 ml of a mixture of acetonitrile and water (75% acetonitrile, 25% water). Gentle heating was required to dissolve the isopropylthioxanthone (35° C.). 86.34 g of Ceric ammonium nitrate (0.1 5748moles) were added in one batch. The reaction was followed by thin layer chromatography (TLC). The reaction mixture was then stirred for 1 hour at room temperature. 400 ml of water was then added and the mixture was extracted with 1000 ml of diethyl ether. The ether layers were combined and dried with magnesium sulphate, and the ether was removed on a rotary evaporator to yield the product.

Product yield 9.92 g (93.32%) of a yellow solid.

The product was analysed by HPLC, LC-MS and IR

EXAMPLE 2

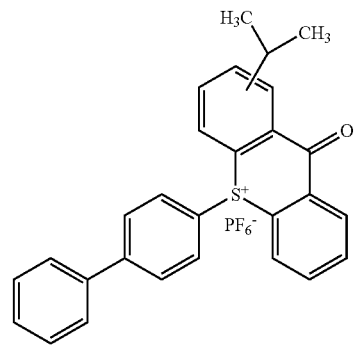

2.025 g (0.0075 moles) of the compound of Example 1, biphenyl (1.604 g, 0.01040 moles), acetic acid (7 ml), dichloromethane (1.75 ml) and acetic anhydride (7 ml) were mixed in round bottomed flask. The temperature of the mixture was reduced to <15° C. using a water/ice bath.

Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator. This yielded 7.17 g of intermediate product. This was dissolved in a minimum of acetic acid. The solution was then poured into a KPF$_6$ solution (4 g in 130 ml water). This appeared to yield a viscous liquid. This was extracted with dichloromethane. The dichloromethane layer was then dried with magnesium sulphate, and the solvent was removed on a rotary evaporator to yield the product. A second extraction was also carried out by dissolving the product in dichloromethane and extracting with water, re-drying the dichloromethane and removing the dichloromethane using a rotary evaporator.

Product yield 4.12 g (99.5%) of a brown pasty solid.
The product was analysed by HPLC, LC-MS and IR

EXAMPLE 3

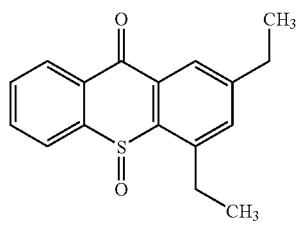

10.0 g (0.03731 moles) of 2,4-diethylthioxanthone (DETX) were dissolved in 630 ml of a mixture of acetonitrile and water (75% acetonitrile, 25% water). Gentle heating was required to dissolve the DETX (45° C.). 81.79 g of Ceric ammonium nitrate (0.1492 moles) were added in one batch. The reaction was followed by TLC. The reaction mixture was stirred for 45 minutes. At this stage TLC indicated that the reaction was complete. The reaction mixture was allowed to cool to room temperature and 400 ml of water was then added. The mixture was extracted with 1000 ml of diethyl ether. The ether layers were combined and dried with magnesium sulphate, and the ether was removed on a rotary evaporator to yield the product. At this stage the product still contained some inorganic residue. The product was therefore re-dissolved in diethyl ether, washed with water and dried with magnesium sulphate. The ether was then removed on a rotary evaporator to yield the product.

Product is a yellow solid, yield not recorded.
The product was analysed by HPLC, LC-MS and IR.

EXAMPLE 4

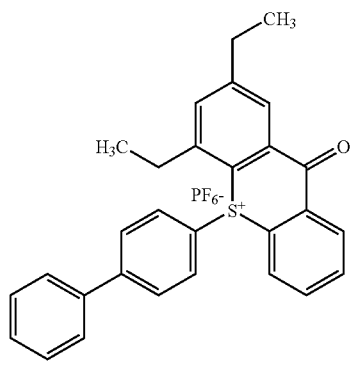

2.0 g (0.00704 moles), DETX sulphoxide from Example 3, biphenyl (1.503 g, 0.0098 moles), acetic acid (7 ml), dichloromethane (1.75 ml) and acetic anhydride (7 ml) were mixed in round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then dried with magnesium sulphate, filtered and removed on a rotary evaporator. This yielded ~4.0 g of intermediate product. This was dissolved in a minimum of acetic acid. The solution was then poured into a KPF$_6$ solution (2 g in 65 ml water). This appeared to yield a viscous liquid. This was extracted with dichloromethane. The dichloromethane layer was washed with 3×100 ml water and then dried with magnesium sulphate, and the solvent was removed on a rotary evaporator to yield the product.

Product yield 2.12 g (53.2%) of a brown pasty solid.

The product was analysed by HPLC, LC-MS and IR.

EXAMPLE 5

Preparation of 2-isopropylthioxanthone sulphoxide

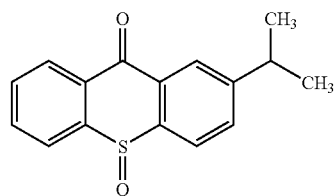

10.0 g (0.03937 moles) of 2-isopropylthioxanthone were dissolved in 630 ml of a mixture of acetonitrile and water (75% acetonitrile, 25% water). Gentle heating was required to dissolve the 2-isopropylthioxanthone (35° C.). The temperature was then allowed to return to room temperature. 86.336 g of Ceric ammonium nitrate (0.15748 moles) were added in one batch. The reaction was followed by TLC. The reaction mixture was stirred for 2.5 hours at room temperature. 400 ml of water was then added and the mixture was extracted with 1000 ml of diethyl ether. The ether layers were combined and dried with magnesium sulphate, and the ether was removed on a rotary evaporator to yield the product. At this stage the product still contained some inorganic residue. The product was therefore re-dissolved in diethyl ether, washed with water and dried with magnesium sulphate. The ether was then removed on a rotary evaporator to yield the product.

Product yield 5.54 g (52.3%) of a yellow solid.
The product was analysed by HPLC, LC-MS and IR

EXAMPLE 6

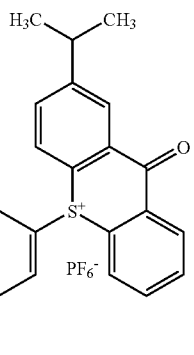

2.025 g 2-isopropylthioxanthone sulphoxide (0.0075 moles) from Example 5, biphenyl (1.604 g, 0.01040 moles), acetic acid (7 ml), dichloromethane (1.75 ml) and acetic anhydride (7 ml) were mixed in a round bottomed flask. The temperature of the mixture was reduced to <5° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200ml (2×100 ml) of dichloromethane. The dichloromethane was then dried with magnesium sulphate, filtered and removed on a rotary evaporator. This yielded 4.0 g of intermediate product. This was dissolved in a minimum of acetic acid. The solution was then poured into a KPF$_6$ solution (2 g in 65 ml water). This appeared to yield a viscous liquid. This was extracted with dichloromethane. The dichloromethane layer was then dried with magnesium sulphate and the solvent was removed on a rotary evaporator to yield the product. There was still an odour of acetic acid. Therefore the product was dissolved in dichloromethane (100 ml), and rewashed with 3×100 ml water. The dichloromethane was dried with magnesium sulphate and filtered, and then the dichloromethane was removed on a rotary evaporator to yield the product.

Product yield 2.54 g (61.2%) of a brown pasty solid.
The product was analysed by HPLC, LC-MS and IR.

EXAMPLE 7

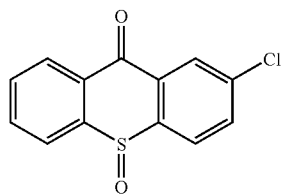

9.71 g of 2-chlorothioxanthone (0.03937 moles) were dissolved in 630 ml of a mixture of acetonitrile and water (75% acetonitrile, 25% water). A further 75 ml of acetonitrile and heating was required to try to dissolve the 2-chlorothioxanthone (65° C.). However, the 2-chlorothioxanthone was still not soluble but the reaction was carried out anyway. 86.336 g of Ceric ammonium nitrate (0.15748 moles) were added in one batch. The reaction was followed by TLC. The reaction mixture was stirred for 90 mins at 65° C. 400 ml of water was then added which crystallised the product. The product was collected by filtration and dried in a vacuum oven.

Product yield 6.96 g (67.3%) of a yellow solid.
The product was analysed by HPLC, LC-MS and IR.

EXAMPLE 8

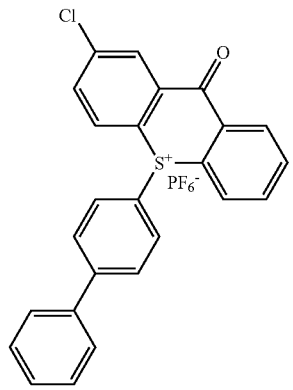

1.97 g 2-Chlorothioxanthone sulphoxide (0.0075 moles) from Example 7, biphenyl (1.604 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator. This yielded 5.39 g of intermediate product. This was dissolved in a minimum of acetic acid. The solution was then poured into a KPF$_6$ solution (2.5 g in 75 ml water). This appeared to yield a viscous liquid. This was extracted with dichloromethane. The dichloromethane layer was then dried with magnesium sulphate and the solvent was removed on a rotary evaporator to yield the product.

Product yield 3.42 g (83.71%) of a brown pasty solid.
The product was analysed by HPLC, LC-MS and IR.

EXAMPLE 9

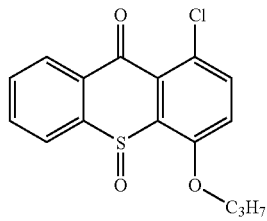

10.0 g (0.0328 moles) of 1-chloro-4-propoxythioxanthone (CPTX) were dissolved in 630 ml of a mixture of acetonitrile and water (75% acetonitrile, 25% water). Gentle heating was required to dissolve the CPTX (50° C.). 71.93 g of Ceric ammonium nitrate (0.1312 moles) were added in one batch.

The reaction was followed by TLC. The reaction mixture was stirred for 1 hour. At this stage TLC indicated that the reaction was complete. The reaction was allowed to cool to room temperature and 400 ml of water added. A small amount of precipitate formed. The mixture was extracted with 1000 ml of diethyl ether. The ether solution was dried with magnesium sulphate, and the ether was removed on a rotary evaporator to yield the product that was subsequently dried in a vacuum oven.

Product yield 6.74 g (72.7%) of a yellow/orange solid.
The product was analysed by HPLC, LC-MS and IR.

EXAMPLE 10

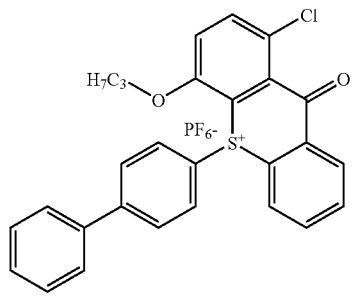

2.4 g (0.0075 moles) of CPTX sulphoxide from Example 9, biphenyl (1.6 g, 0.0104 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then dried with magnesium sulphate and filtered, and the solvent was removed on a rotary evaporator. This yielded ~4.0 g of intermediate product. This was dissolved in a minimum of acetic acid. The solution was then poured into a KPF$_6$ solution (2 g in 65 ml water). A viscous residue was obtained which was extracted into dichloromethane. The dichloromethane layer was washed with water (3×100 ml) and dried with magnesium sulphate, and then the dichloromethane was removed on a rotary evaporator to yield the product. The product is a dark brown viscous material which becomes more crystalline on standing.

Product yield 2.4 g (44.3%) of a brown pasty solid.
The product was analysed by HPLC, LC-MS and IR.

EXAMPLE 11

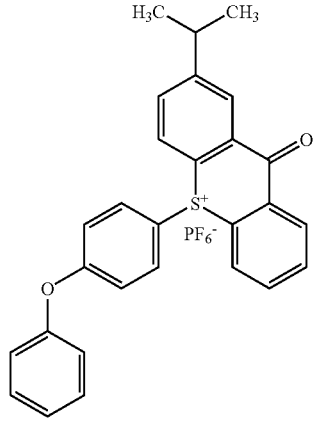

(2.025 g, 0.0075 moles), 2-isopropylthioxanthone sulphoxide from Example 5, diphenyl ether (1.768 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure he temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator. This yielded 6.21 g of intermediate product. This was dissolved in a minimum of acetic acid. The solution was then poured into a KPF$_6$ solution (2.6 g in 85 ml water). This appeared to yield a viscous liquid. This was extracted with dichloromethane. The dichloromethane layer was then dried with magnesium sulphate and the solvent was removed on a rotary evaporator to yield the product.

Product yield 4.23 g (99.3%) of an orange pasty solid.
The product was analysed by HPLC, LC-MS and IR.

EXAMPLE 12

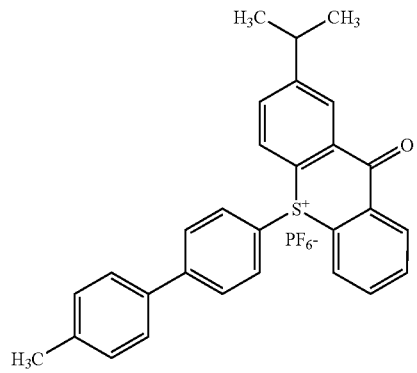

(2.025 g, 0.0075 moles), 2-isopropylthioxanthone sulphoxide from Example 5, 4-methyl biphenyl (1.75 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator. This yielded 5.21 g of intermediate product. This was dissolved in a minimum of acetic acid. The solution was then poured into a KPF$_6$ solution (2.5 g in 75 ml water). This appeared to yield a viscous liquid. This was extracted with dichloromethane. The dichloromethane layer was then dried with magnesium sulphate and the was solvent removed on a rotary evaporator to yield the product.

Product yield 2.69 g (63.4%) of a brown pasty solid.
The product was analysed by HPLC, LC-MS and IR.

EXAMPLE 13

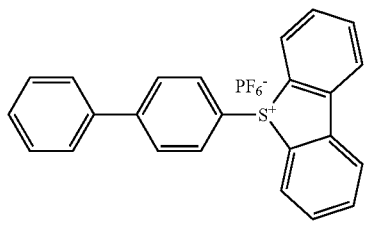

1.5 g Dibenzothiophene sulphoxide (0.0075 moles), biphenyl (1.604 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator. This yielded 4.41 g of intermediate product. This was dissolved in a minimum of acetic acid. The solution was then poured into a $KPF_6$ solution (2.5 g in 75 ml water). The product crystallised from solution and was collected by filtration, washed with water and dried in a vacuum oven.

Product yield 3.04 g (84.1%) of a light brown solid.
The product was analysed by HPLC, LC-MS and IR.

EXAMPLE 14

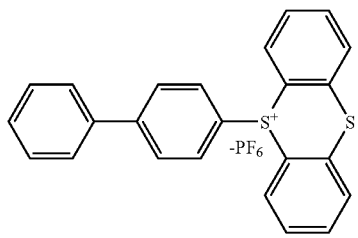

Thianthrene sulphoxide (2.0 g, 0.0086 moles), biphenyl (1.86 g, 0.012 moles), acetic acid (7 ml), dichloromethane (1.75 ml) and acetic anhydride (7 ml) were mixed in a round bottomed flask. A further 5 ml of dichloromethane was added to dissolve the thianthrene sulphoxide. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then dried with magnesium sulphate, filtered and removed on a rotary evaporator. This yielded 4.0 g of intermediate product. This was dissolved in a minimum of acetic acid. The solution was then poured into a $KPF_6$ solution (2 g in 65 ml water). The product produced was a solid that was collected by filtration and washed with water. Finally, the product was dried in a vacuum oven.

Product yield 3.42 g (77.1%) of a very pale pink solid.
The product was analysed by HPLC, LC-MS and IR.

EXAMPLE 15

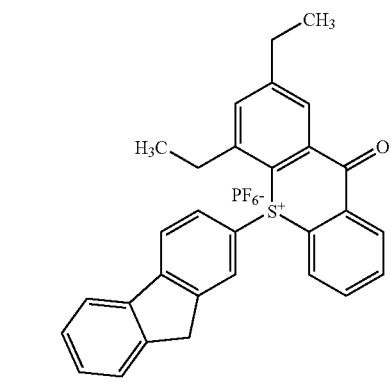

2.0 g (0.00704 moles), 2,4-diethylthioxanthone sulphoxide from Example 3, fluorene (1.63 g, 0.0098 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then dried with magnesium sulphate, filtered and removed on a rotary evaporator. This yielded ~4.0 g of intermediate product. This was dissolved in a minimum of acetic acid. The solution was then poured into a $KPF_6$ solution (2 g in 65 ml water). This appeared to yield a viscous liquid. This was extracted with dichloromethane. The dichloromethane layer was washed with 3×100 ml water and then dried with magnesium sulphate, and the solvent was removed on a rotary evaporator to yield the product Product yield 2.31 g (53.8%) of a brown solid.
The product was analysed by HPLC, LC-MS and IR

EXAMPLE 16

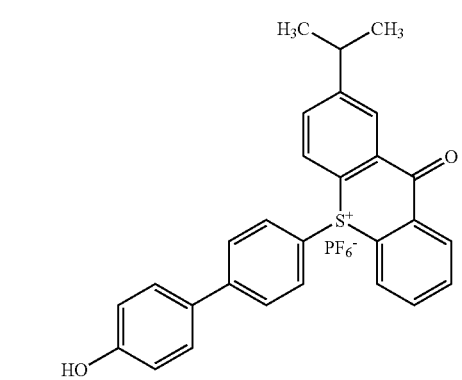

(2.025 g, 0.0075 moles), 2-isopropylthioxanthone sulphoxide from Example 5, 4-hydroxybiphenyl (1.768 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition ws complete, the mixture was stirred for 2 hours, allowing the temperature to increase to room temperature. 100 ml of water was then added to the mixture. This was then extracted with -200 ml (2×100 ml) of dichloromethane. The dichloromethane was then removed on a rotary evaporator. This yielded 5.91 g of intermediate product. This was dissolved in a minimum of acetic acid. The solution was then poured into a $KPF_6$ solution (2.5 g in 75 ml water). This appeared to yield a viscous liquid. This was extracted with dichloromethane. The dichloromethane layer was then dried with magnesium sulphate and the solvent was removed on a rotary evaporator to yield the product. A second extraction was carried out to purify the product further as there was still a strong odour of acetic acid.

Product is a brown solid, yield not recorded The product was analysed by HPLC, LC-MS and IR. Analysis suggests product is a mixture of hydroxy and acetyl biphenyl derivatives (produced under the conditions of the reaction).

COMPARATIVE EXAMPLE 1

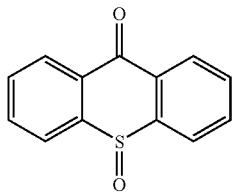

8.35 g of Thioxanthone (0.03937 moles) were dissolved in 630 ml of a mixture of acetonitrile and water (75% acetonitrile, 25% water). A further 75 ml of acetonitrile was added in an unsuccessful attempt to dissolve the thioxanthone. The mixture was heated to 55° C. 86.336 g of Ceric ammonium nitrate (0.15748 moles) was added, and the reaction was carried out, followed by thin layer chromatography (TLC). The reaction mixture was stirred for 90 mins at 55° C. 400 ml of water was then added which, when cooled, resulted in the product crystallising from solution. The crystals were remove by filtration and then dried in a vacuum oven.

Product yield 7.23 g (80.54%) of a yellow solid.

The product was analysed by HPLC, LC-MS and IR

COMPARATIVE EXAMPLE 2

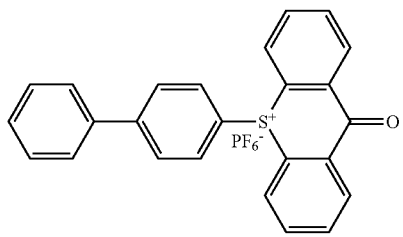

1.71 g (0.0075 moles) of thioxanthone sulphoxide from Comparative Example 1, 1.604 g biphenyl (0.01040 moles), acetic acid (7 ml), dichloromethane (1.75ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator to give 5.17 g of intermediate product. This was dissolved in a minimum of acetic acid. The solution was then poured into a KPrt solution (2.5 g in 75 ml water). The product crystallised from solution and was collected by filtration, washed with water and then dried in a vacuum oven.

Product yield 2.38 g (62.2%) of a brown solid.

The product was analysed by HPLC, LC-MS and IR

COMPARATIVE EXAMPLE 3

ATTEMPTED SYNTHESIS

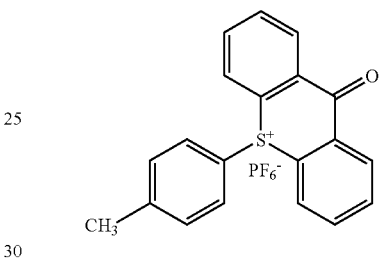

1.71 g (0.0075 moles) of thioxanthone sulphoxide from Comparative Example 1, 0.96 g toluene (0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator to give 1.51 g of intermediate product. This was dissolved in a minimum of acetic acid. The solution was then poured into a $KPF_6$ solution (2 g in 65 ml water). The product crystallised from solution and was collected by filtration, washed with water and then dried in a vacuum oven.

Product yield 0.48 g of a brown solid.

The product was analysed by HPLC, LC-MS and IR and found not to have produced any product. Analysis suggests the isolated product is still the thioxanthone sulphoxide starting material.

COMPARATIVE EXAMPLE 4

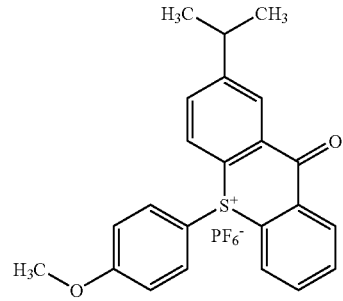

Isopropylthioxanthone sulphoxide (2.025 g, 0.0075 moles) from Comparative Example 1, anisole (1.1232 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then removed on a rotary evaporator. This yielded 10.0 g of intermediate product. This was dissolved in a minimum of acetic acid. The solution was then poured into a $KPF_6$ solution (4 g in 130 ml water). This appeared to yield a viscous liquid. This was extracted with dichloromethane. The dichloromethane layer was then dried with magnesium sulphate, and the solvent was removed on a rotary evaporator to yield the product.

Product yield 2.88 g (75.9%) of a brown viscous liquid. The product was analysed by HPLC, LC-MS and IR

COMPARATIVE EXAMPLE 5

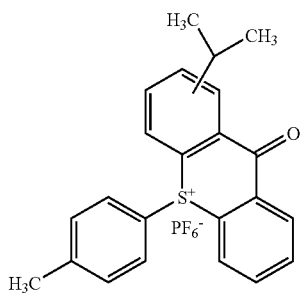

Isopropylthioxanthone sulphoxide (2.025 g, 0.0075 moles) from Comparative Example 1, toluene (0.9568 g, 0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added drop wise, making sure the temperature did not exceed 15° C. After the addition was complete, the mixture was stirred for 2 hours, allowing the temperature to increase to room temperature. 100 ml of water was then added to the mixture. This was then extracted with ~200 ml (2×100 ml) of dichloromethane. The dichloromethane was then dried with magnesium sulphate and the dichloromethane then removed on a rotary evaporator. This yielded 2.72 g of intermediate product. This was dissolved in a minimum of acetic acid. The solution was then poured into a $KPF_6$ solution (2 g in 65 ml water). This appeared to yield a viscous liquid. This was extracted with dichloromethane. The dichloromethane layer was then dried with magnesium sulphate and the solvent was removed on a rotary evaporator to yield the product.

Product yield 2.28 g (62.04%) of a brown viscous liquid. The product was analysed by HPLC, LC-MS and IR.

EXAMPLE 17

Varnish Formulations.

The following varnish formulations were used in the evaluation experiments.

| Material Code/ Description | Standard Varnish 1 | Standard Varnish 2 | Experimental Varnish 1 | Experimental Varnish 2 |
|---|---|---|---|---|
| Uvacure 1500 | 91.8 | 87.8 | 95.8 | 91.8 |
| Tegorad 2100 | 0.2 | 0.2 | 0.2 | 0.2 |
| Propylene carbonate | — | 4.0 | — | 4.0 |
| Uvacure 1592* | 8.0 | 8.0 | — | — |
| Experimental Photoinitiator | — | — | 4.0 | 4.0 |
| Total | 100.0 | 100.0 | 100.0 | 100.0 |

Uvacure 1592 is a standard photoinitiator from UCB (supplied as a 50% solution in propylene carbonate.)

Uvacure 1500 is a cycloaliphatic epoxide monomer from UCB.

Tegorad 2100 is a wetting aid from TEGO.

Summary of Curing Experiments.

The varnishes were printed onto Leneta opacity charts using a No. 1 K-bar and draw down pad. The prints were passed through a UV curing rig fitted with a medium pressure mercury arc lamp at 80 m/min. The UV lamp power is 280 watts/inch.

Standard Varnish formulations 1 & 2, containing the photoinitiator Uvacure 1592 cure with one pass at the UV rig conditions stated above. However, the photoinitiator Uvacure 1592 is only completely soluble with additional propylene carbonate (Standard Varnish formulation 2). Colour on cure is good but there is a very strong diphenyl sulphide odour.

| | | | Curing Results Summary | | | |
|---|---|---|---|---|---|---|
| | | | Number of passes to cure | | | |
| Initiator Code | Initiator Description | Soluble | Experimental varnish 1 (No propylene carbonate) | Experimental varnish 2 (4% propylene carbonate) | Odour | Colour of film |
| Comparative Example 5 | ITX/ Toluene | Yes | >15 | 9 | No | Slightly Yellow |
| Comparative Example 4 | ITX/ Anisole | Yes | 10 | 2–3 | No | Slightly Yellow |
| Example 2 | ITX/ Biphenyl | Yes | 1 | 1 | No | Slightly Yellow |

-continued

| Initiator Code | Initiator Description | Soluble | Experimental varnish 1 (No propylene carbonate) | Experimental varnish 2 (4% propylene carbonate) | Odour | Colour of film |
|---|---|---|---|---|---|---|
| Comparative Example 2 | TX/Biphenyl | No | 1 | 1 | No | Slightly Yellow |
| Example 8 | CTX/Biphenyl | No | 1–2 | 1 | No | Slightly Yellow |
| Example 6 | 2-ITX/Biphenyl | Yes | 1 | 1 | No | Slightly Yellow |
| Example 4 | DETX/Biphenyl | Yes | 1 | 1 | No | Slightly Yellow |
| Example 13 | Dibenzo-thiophene/Biphenyl | No | 1–2 | 1 | No | None |
| Example 12 | 2-ITX/4-Methyl-biphenyl | Yes | 2 | 1 | No | Slightly Yellow |
| Example 16 | 2-ITX/4-Hydroxy-biphenyl | Yes | >6 | 2–3 | No | Slightly Yellow |
| Example 11 | 2-ITX/Diphenyl ether | Yes | 1 | 1 | No | Slightly Yellow |
| Example 10 | CPTX/Biphenyl | No | >7 | 2 | No | Very Yellow |
| Example 14 | Thianthrene/Biphenyl | Yes | 1 | 1 | No | None |
| Example 15 | DETX/Fluorene | No | 3 | 2–3 | No | Slightly Yellow |

EXAMPLE 18

Evaluation Results for Example 6 in UV Flexo Inks

Ink formulation.

| Ingredient | Yellow test | Yellow Std | Magenta Test | Magenta Std | Cyan Test | Cyan Std | Black Test | Black Std |
|---|---|---|---|---|---|---|---|---|
| Pigment Concentrate | 44.0 | 44.0 | 56.8 | 56.8 | 54.0 | 54.0 | 70.0 | 70.0 |
| TMPO | 39.6 | 39.6 | 30.3 | 30.3 | 33.0 | 33.0 | 22.0 | 22.0 |
| Uvacure 1500 | 8.4 | 8.4 | 4.9 | 4.9 | 4.7 | 4.7 | — | — |
| Uvacure 1592 | 8.0 | — | 8.0 | — | 8.0 | — | 8.0 | — |
| Example 6 (50% solids in Uvacure 1500) | — | 8.0 | — | 8.0 | — | 8.0 | — | 8.0 |

Uvacure 1592, a triaryl sulphonium salt photoinitiator from UCB, was supplied at 50% solids in propylene carbonate.

TMPO is trimethylolpropane oxetane from Perstorp

Cure and Test Conditions

The inks were printed on SWH-30, BOPP film from Hoechst, using the Easiproof hand held flexo proofer with anilox tool 41. The prints were cured under a medium pressure mercury arc lamp at a belt speed of 80 m/min with a lamp power of 120 W/cm.

The inks were assessed for MEK resistance, scratch, thumb twist and adhesion. The MEK resistance was assessed immediately after cure and 3 days later. The test ink and the standard were printed side-by-side and alone.

Cure Results.

All formulations were found to cure with a single pass under the UV lamp with the conditions described.

| Printing conditions | Ink | Yellow | | | | |
|---|---|---|---|---|---|---|
| | | MEK | | Scratch | Thumb Twist | Adhesion |
| | | Immediate | 3 Days | | | |
| Side by side | Std | 23 | 62 | ✓ | ✓ | 100% |
| | Test | 10 | 35 | ✓ | ✓ | 100% |
| Alone | Std | 6 | 31 | ✓ | ✓ | 100% |
| | Test | 6 | 24 | ✓ | ✓ | 100% |

Magenta

| Printing conditions | Ink | MEK Immediate | MEK 3 Days | Scratch | Thumb Twist | Adhesion |
|---|---|---|---|---|---|---|
| Side by side | Std | 2 | 32 | ✓ | ✓ | 100% |
| | Test | 5 | 17 | Inferior, As std after 90 s | ✓ | 100% |
| Alone | Std | 6 | 17 | ✓ | ✓ | 100% |
| | Test | 2 | 12 | Inferior, As std after 90 s | Inferior, as std after 30 s | 100% |

Cyan

| Printing conditions | Ink | MEK Immediate | MEK 3 Days | Scratch | Thumb Twist | Adhesion |
|---|---|---|---|---|---|---|
| Side by side | Std | 3 | na | ✓ | ✓ | 100 |
| | Test | 2 | na | ✓ | ✓ | 100 |
| Alone | Std | 4 | na | ✓ | ✓ | 100% (Slow) 0% jerky |
| | Test | 2 | na | ✓ | ✓ | 100 |

Black

| Printing conditions | Ink | MEK Immediate | MEK 3 Days | Scratch | Thumb Twist | Adhesion |
|---|---|---|---|---|---|---|
| Side by side | Std | 3 | 21 | ✓ | ✓ | 0% |
| | Test | 1 | 9 | ✓ | ✓ | 0% |
| Alone | Std | 4 | 21 | After 30 s | ✓ | Slow 100% Jerky 0% |
| | Test | 2 | 10 | After 30 s | ✓ | Slow 100% Jerky 0% |

EXAMPLE 19

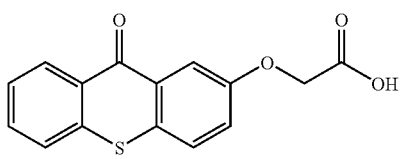

24 g sodium hydroxide was refluxed in 400 ml tetrahydrofuran for five minutes. 22.8 g (0.1 mols) hydroxythioxanthone was added and reflux continued for 1 hour, during which time the colour changed to bright red, indicating the formation of the sodium salt of hydroxythioxanthone. 35.1 g (0.21 mols) of ethyl bromoacetate was added and reflux was continued for three hours. After cooling to room temperature, 400 ml of deionised water were added with stirring, and the tetrahydrofuran was distilled out to yield a clear red solution. Reflux was continued for a further 2 hours in order to hydrolyse all the ester intermediate. The solution was then cooled to 50° C. and 400 ml 1.0 M aqueous hydrochloric acid was added with stirring, causing the solid product to precipitate out. After refluxing for five minutes to be sure that all the sodium salt was converted to free acid, the solution was cooled to room temperature and stirred for two hours before filtering off the solid, washing with 400 ml deionised water and drying in a vacuum oven at 80 C.

Product yield 28.12 g (97%). Product analysed by NMR.

EXAMPLE 20

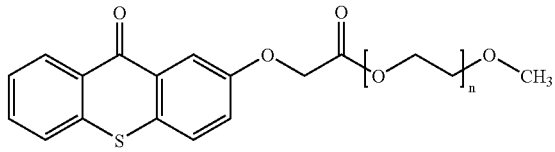

18.0 g (0.063 mols) carboxymethoxythioxanthone from Example 19 and 19.6 g (0.056 mols) of polyethylene glycol methyl ether (350 molecular weight) were azeotropically refluxed under nitrogen in 200 ml toluene with 0.6 g p-toluenesulphonic acid monohydrate catalyst. After 10 hours, the solution was cooled to 35° C. and washed twice with 100 ml 10% aqueous potassium carbonate solution and 100 ml deionised water before drying over anhydrous magnesium sulphate. The solution was filtered and all solvent was removed on a rotary evaporator to yield an orange oil.

Product yield 25.47 g (73.6%). Product analysed by HPLC and IR

EXAMPLE 21

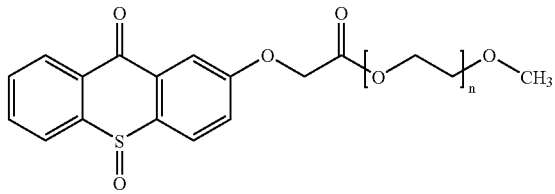

5.0 g of the product from Example 20 (0.0080906 moles) were dissolved in 129.5 ml of acetonitrile/water (75:25). 17.74 g (0.03236 moles) of CAN were added in one batch. The reaction mixture was stirred for 1 hour at room temperature. 82 ml of water was then added. The mixture was then extracted with 3×50 ml of dichloromethane. The organic extracts were combined and dried with magnesium sulphate and then filtered. The solvent was removed on a rotary evaporator to yield the product.

Product yield 5.00 g (97.5%) of a yellow liquid. The product was analysed by FT-IR and HPLC.

EXAMPLE 22

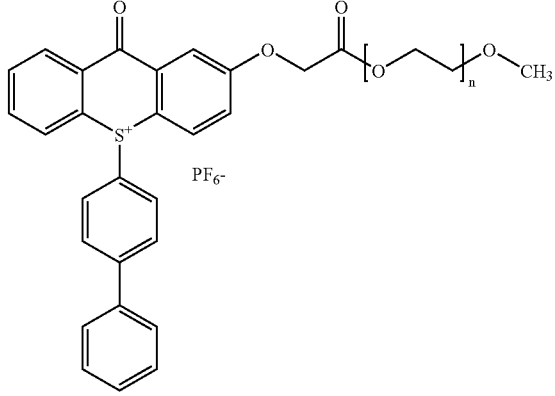

4.0 g of the product from Example 21 (0.0063091 moles), biphenyl (0.972 g, 0.00631 moles) and acetic anhydride (5.2 ml) were mixed in a round bottomed flask. The temperature of the mixture was reduced to approx. 10° C. using a water/ice bath. Conc. Sulphuric acid (1.97 g) was then added drop-wise making sure that the temperature did not exceed 20° C. The mixture was then added drop-wise to a solution of 1.37 g potassium hexafluoro phosphate ($KPF_6$) in water 8.52 g/methanol 10.1 g. 2 ml of methanol was also used to wash out the reaction vessel and added to the methanol/water/$KPF_6$ solution. The mixture was then stirred at 35–40° C. for 30 minutes. The mixture was then cooled to 10° C. and stirred for a further 30 minutes. No product crystallised. Therefore, 50 ml of MEK and 50 ml of water were added but separation did not occur. 75 ml of DCM were added to extract the product and then a further 30 ml of DCM. The DCM extracts were combined and dried with magnesium sulphate. The DCM was then filtered and finally removed on a rotary evaporator to yield the product.

Product yield 5.94 g of a viscous brown liquid/paste. The product was analysed by FT-IR and HPLC.

EXAMPLE 23

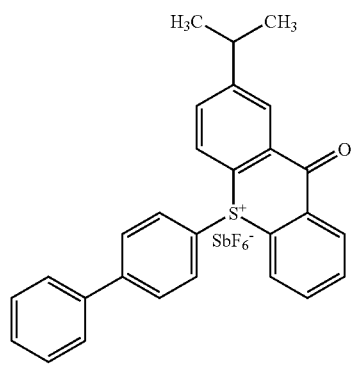

5 g of the product of Example 5 (0.01852 moles), biphenyl (2.852 g, 0.01852 moles) and acetic anhydride (15.12 g) were mixed in a round bottomed flask. The temperature of the mixture was reduced to <10° C. using a water/ice bath. Concentrated sulphuric acid (5.79 g) was then added drop wise, making sure the temperature did not exceed 20° C. After the addition was complete, the mixture was added to a solution of methanol (29.5 g), water (25.0 g) and $KSbF_6$ (5.97 g). The mixture was then stirred at 35–40° C. for 30 minutes. The mixture was then cooled to <10° C. using an ice/water bath and stirring continued for a further 30 minutes. The precipitate was collected by filtration and washed with 50 ml of water. The material was then dried in the vacuum oven at 40° C. for 4 hours.

Product yield 8.85 g (74.34%) of a brown solid. The product was analysed by HPLC and IR.

EXAMPLE 24

Varnish Formulations.

The following varnish formulations were used in the evaluation experiments.

| Material Code/Description | Standard Varnish | Experimental Varnish |
|---|---|---|
| Uvacure 1500 | 91.8 | 95.8 |
| Tegorad 2100 | 0.2 | 0.2 |
| Propylene carbonate | — | — |
| Uvacure 1592 | 8.0 | — |
| Experimental Photoinitiator | — | 4.0 |
| Total | 100.0 | 100.0 |

Uvacure 1592 is a standard photoinitiator from UCB (supplied as a 50% solution in propylene carbonate).

Uvacure 1500 is a cycloaliphatic epoxide monomer from UCB.

Tegorad 2100 is a wetting aid from TEGO

Summary of Curing Experiments.

The varnishes were printed onto Leneta opacity charts using a No.0 K-bar and draw down pad. The prints were passed through a Primarc Maxicure UV curing rig fitted with a medium pressure mercury arc lamp at 80 m/min. The UV lamp power is 300 Watts/inch and was run at a half power setting to aid product differentiation.

| Initiator Code | Initiator Description | Soluble | No. passes to cure | Odour | Colour |
|---|---|---|---|---|---|
| Uvacure 1592 | Standard triarylsulphonium salt | With difficulty | 1 | Strong (diphenyl sulphide) | Colourless |
| Example 22 | PEG350CMTX/Biphenyl $PF_6$ | Yes | 2 | No | Slightly Yellow |
| Example 23 | 2-ITX/Biphenyl $SbF_6$ | Yes | 1 | No | Slightly Yellow |

These results demonstrate that the experimental photoinitiators of the present invention have cure speed similar to those of one of the best available commercial standard photoinitiators. Solubility and odour on cure are superior to that of the standard photoinitiator.

EXAMPLE 25

GC-MS Headspace Analysis

The following varnish formulations were used in the evaluation experiments.

| Material Code/Description | Sulphonium salt formulations | Iodonium salt formulation |
|---|---|---|
| Uvacure 1500 | 75 | 77.5 |
| TMPO | 20.9 | 18.9 |
| Tegorad 2100 | 0.1 | 0.1 |
| Propylene carbonate | 2 | — |
| Photoinitiator | 2 | 1.5 |
| Esacure KIP 150 | — | 2 |

The standard photoinitiators used were Uvacure 1592 (triarylsulphonium salt photoinitiator from UCB, supplied as a 50% solution in propylene carbonate) and IGM 440 (diaryliodonium salt photoinitiator from IGM.

Uvacure 1500 is a cycloaliphatic epoxide monomer from UCB.

Tegorad 2100 is a wetting aid from TEGO.

TMPO is a monofunctional oxetane alcohol diluent from Perstorp.

Esacure KIP 150 is a hydroxyalkylphenone photoinitator from Lamberti.

The varnishes were printed onto aluminium foil using a No.0 K-bar and draw down pad. The prints were passed twice through a Primarc Maxicure UV curing rig fitted with a 300 Watts/inch medium pressure mercury arc lamp at 80 m/min. Under these conditions the samples were over-cured, which was desirable in order to maximise the amount of by-product formation. 200 cm2 of each sample was placed in a sealed tube and subjected to a standard headspace analysis procedure where they are heated to 200° C. for 10 minutes and then the headspace volume transferred to a gas chromatograph fitted with a mass spectrometer detector via a heated transfer line.

The compounds detected in these analyses are shown below. No attempt was made to quantify individual materials. Note that there were also several peaks common to all samples that derive from the Uvacure 1500.

| Photoinitiator | Materials detected in Head-space proceedure |
|---|---|
| Uvacure 1592 | Diphenyl sulphide |
| | Several small unidentified peaks* |
| IGM 440 | Toluene |
| | Iodobenzene |
| | Several unidentified peaks |
| Example 6 | Biphenyl |

*Benzene would also be expected from this analysis but was not seen due to the solvent delay used in this standard GC method.

These results demonstrate that for Example 6, the only photoinitiator byproduct detected is biphenyl, which is of limited toxicological concern for food packaging inks as it is itself an approved food additive material. This is in contrast with the undesirable materials released from the 2 standard photoinitiators.

The invention claimed is:

1. Compounds of formula (I):

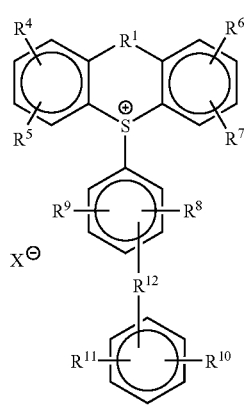

(I)

in which:

$R^1$ represents a direct bond, an oxygen atom, a group >$CH_2$, a sulphur atom, a group >C=O, a sulphur atom, a group >C=O, a group —$(CH_2)_2$— or a group of formula —N—$R^a$, where $R^a$ represents a hydrogen atom or a $C_1$–$C_{12}$ alkyl group having from 1 to 12 carbon atoms;

$R^4$, $R^5$, $R^6$ and $R^7$ are independently selected from hydrogen atoms and substituents, defined below, provided that, when $R^1$ represents a group >C=O, then at least one of $R^4$, $R^5$, $R^6$ and $R^7$ represents a substituent;

$R^8$, $R^9$, $R^{10}$ and $R^{11}$ are independently selected from hydrogen atoms, hydroxy groups, and $C_1$–$C_4$ alkyl groups;

or $R^9$ and $R^{11}$ are joined to form a fused ring system with the benzene rings to which they are attached;

$R^{12}$ represents a direct bond, an oxygen atom or a —$CH_2$— group;

said substituents are: a $C_1$–$C_{20}$ alkyl group, a $C_1$–$C_{20}$ alkoxy group, a $C_2$–$C_{20}$ alkenyl group, a halogen atom, a nitrile group, a hydroxyl group, a $C_6$–$C_{10}$ aryl group, a $C_7$–$C_{13}$ aralkyl group, a $C_6$–$C_{10}$ aryloxy group, a $C_7$–$C_{13}$ aralkyloxy group, a $C_8$–$C_{12}$ arylalkenyl group, a $C_3$–$C_8$ cycloalkyl group, a carboxy group, a $C_2$–$C_7$ carboxyalkoxy group, a $C_2$–$C_7$ alkoxycarbonyl group, a $C_7$–$C_{13}$ aryloxycarbonyl group, a $C_2$–$C_7$ alkylcarbonyloxy group, a $C_1$–$C_6$ alkanesulphonyl group, a $C_6$–$C_{10}$ arenesulphonyl group, a $C_1$–$C_6$ alkanoyl group or a $C_7$–$C_{11}$ arylcarbonyl group; and $X^-$ represents an anion, provided $X^-$ does not represent an alkoxy, hydroxyalkoxy or aryloxy group, or perchlorate group, when $R^1$ represents a direct bond;

provided that $R^1$ is not a sulphur atom when $R^3$ is OH in the ortho position of the ring, $R^4$ through $R^{11}$ are hydrogen, $R^{12}$ is a direct bond in either meta position of the ring containing $R^9$, and X is perchlorate; and or an esters thereof.

2. The compound according to claim 1, in which $R^4$, $R^5$, $R^6$ and $R^7$ are independently selected from hydrogen atoms, $C_1$–$C_{10}$ alkyl groups, a $C_1$–$C_{10}$ alkoxy groups, halogen atoms, and $C_3$–$C_8$ cycloalkyl groups.

3. The compound according to claim 1, in which three or four of $R^4$, $R^5$, $R^6$ and $R^7$ represent hydrogen atoms.

4. The compound according to claim 3, in which one or more of $R^4$, $R^5$, $R^6$ and $R^7$ represents an ethyl or isopropyl group.

5. The compound according to claim 1, in which two, three or four of $R^8$, $R^9$, $R^{10}$ and $R^{11}$ represent hydrogen atoms.

6. The compound according to claim 1, in which all of $R^8$, $R^9$, $R^{10}$ and $R^{11}$ represent hydrogen atoms.

7. The compound according to claims 1, in which $R^1$ represents a group >C=O, a sulphur atom or a direct bond.

8. The compound according to claim 7, in which $R^1$ represents a group >C=O.

9. The compound according to claim 1, in which that part of the compound of formula (I) having the formula (A):

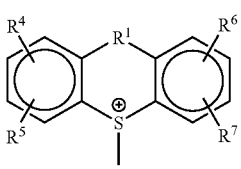

(A)

is a residue of substituted or unsubstituted thianthrene, dibenzothiophene, thioxanthone, thioxanthene, phenoxathiin phenothiazine or N-alkylphenothiazine.

10. The compound according to claim 9, in which said residue is substituted thioxanthone.

11. The compound according to claim 9, in which said residue is substituted or unsubstituted thianthrene.

12. The compound according to claim 9, in which said residue is substituted dibenzothiophene.

13. The compound according to claim 9, in which said residue is substituted or unsubstituted phenoxathiin.

14. The compound according to claim 9, in which said residue is substituted or unsubstituted phenothiazine or N-alkylphenothiazine.

15. The compound according to claim 1, in which:

$R^4$, $R^5$, $R^6$ and $R^7$ are individually the same or different and each represents a hydrogen atom or an alkyl group having from 1 to 4 carbon atoms;

$R^{12}$ represents a direct bond; and $R^8$, $R^9$, $R^{10}$ and $R^{11}$ represent hydrogen atoms.

16. The compound according to claim 1, in which $X^-$ represents a $PF_6^-$, $SbF_6^-$, $AsF_6^-$, $BF_4^-$, $B(C_6F_5)_4^-$, $R^aB(Ph)_3^-$ (where $R^a$ represents a $C_1$–$C_6$ alkyl group and Ph represents a phenyl group), $R^bSO_3^-$ (where $R^b$ represents a $C_1$–$C_6$ alkyl or haloalkyl group or an aryl group), or $ArSO_3^-$ (where Ar represents an aryl group) group.

17. The compound according to claim 16, in which $X^-$ represents a $PF_6^-$, $SbF_6^-$, $AsF_6^-$, $BF_4^-$, $CF_6SO_3^-$, $BF_4^-$ group.

18. The compound according to claim 17, in which $X^-$ represents a $PF_6^-$ group.

19. The compound according to claim 1, having the formula:

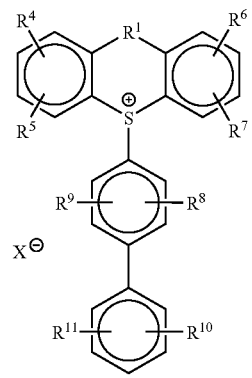

(Ia)

in which $R^1$, $R^4$, $R^5$, $R^6$, $R^7$, $R^8$, $R^9$, $R^{10}$, $R^{11}$ and $X^-$ are as defined in claim 1.

20. The compound according to claim 4, in which at least two of $R^8$, $R^9$, $R^{10}$ and $R^{11}$ represent hydrogen atoms; $R^1$ represents a group >C=O, a sulphur atom or a direct bond; and $X^-$ represents a $PF_6^-$, $SbF_6^-$, $AsF_6^-$, $BF_4^-$, $CF_6SO_3^-$, $BF_4^-$ group.

21. An energy-curable composition comprising: (a) a polymerisable monomer, prepolymer or oligomer; and (b) a photoinitiator which is a compound of formula (I), as claimed in any one of claims 1, 8, 9, 15, 19 and 20.

* * * * *